United States Patent
Bolscher et al.

(10) Patent No.: US 9,133,238 B2
(45) Date of Patent: Sep. 15, 2015

(54) USE OF PEPTIDES FOR PROMOTING WOUND HEALING

(75) Inventors: Johannes Gerhardus Maria Bolscher, Amsterdam (NL); Arie Van Nieuw Amerongen, Amsterdam (NL); Engelmundus Cornelis Ignatius Veerman, Amsterdam (NL); Menno Johannes Oudhoff, Amsterdam (NL); Willem Van't Hof, Amsterdam (NL); Kamran Nazmi, Amsterdam (NL); Petronella Adriana Maria Van Den Keijbus, Amsterdam (NL)

(73) Assignee: Rapid Pathogen Screeening, Inc., Sarasota, FL (US)

( * ) Notice: Subject to any disclaimer, the term of this patent is extended or adjusted under 35 U.S.C. 154(b) by 546 days.

(21) Appl. No.: 12/811,928

(22) PCT Filed: Jan. 7, 2009

(86) PCT No.: PCT/EP2009/000241
§ 371 (c)(1),
(2), (4) Date: Oct. 4, 2010

(87) PCT Pub. No.: WO2009/087117
PCT Pub. Date: Jul. 16, 2009

(65) Prior Publication Data
US 2011/0178010 A1    Jul. 21, 2011

(30) Foreign Application Priority Data

Jan. 7, 2008 (EP) ................................. 08075012
Oct. 30, 2008 (NL) ................................. 2002152

(51) Int. Cl.
*C07K 7/00* (2006.01)
*C07K 14/00* (2006.01)
*A61K 38/17* (2006.01)
*A61K 38/18* (2006.01)
*C07K 14/47* (2006.01)

(52) U.S. Cl.
CPC ............... *C07K 7/00* (2013.01); *A61K 38/1729* (2013.01); *A61K 38/18* (2013.01); *C07K 14/00* (2013.01); *C07K 14/4702* (2013.01)

(58) Field of Classification Search
CPC .................................. C07K 7/00; C07K 14/00
USPC ........... 530/324, 325, 326; 514/2.3, 3.3, 21.3, 514/21.4
IPC ............. C07K 4/00, 14/00; A61K 38/00, 38/04, A61K 38/16
See application file for complete search history.

(56) References Cited

U.S. PATENT DOCUMENTS

| | | | |
|---|---|---|---|
| 5,486,503 A | 1/1996 | Oppenheim et al. | |
| 5,631,228 A | 5/1997 | Oppenheim et al. | |
| 5,646,119 A * | 7/1997 | Oppenheim et al. | ........... 514/2.4 |
| 5,912,230 A | 6/1999 | Oppenheim et al. | |
| 6,086,863 A | 7/2000 | Ritter et al. | |
| 6,462,070 B1 | 10/2002 | Hasan et al. | |
| 6,555,650 B1 | 4/2003 | Lajoie et al. | |
| 2006/0222635 A1* | 10/2006 | Centanni et al. | ........... 424/93.21 |

FOREIGN PATENT DOCUMENTS

| | | | |
|---|---|---|---|
| CA | 2285673 A1 | 4/2001 | |
| EP | 0721774 B1 | 7/1996 | |
| JP | 03261717 A | 11/1991 | |
| JP | 04182420 A | 6/1992 | |
| JP | 06234653 A | 8/1994 | |
| JP | 06-287146 | * 10/1994 | |
| JP | 07258110 A | 10/1995 | |
| WO | 03079997 A2 | 10/2003 | |
| WO | 2008134882 A1 | 11/2008 | |

OTHER PUBLICATIONS

Abstract of JP 1993/0045998 (1995).*
Troxler, et al.,"Structural Relationship between Human Salivary Histatins," Journal of Dental Research, 1990, pp. 2-06, vol. 69, No. 1, International Association for Dental Research, US.
Perinpanayagam, et al.,"Characterization of low-molecular-weight peptides in human parotid saliva," Journal of Dental Research, 1995, pp. 345-350, vol. 74, No. 1.
Murakami, et al.,"Histatin as a Synergistic Stimulator with Epidermal Growth Factor of Rabbit Chondrocyte Proliferation," Biochemical and Biophysical Research Communications, 1994, pp. 274-280, vol. 198, No. 1, Academic Press Inc., Orlando, FL, US.
"Burning mouth syndrome", 2 pages, dated Jul. 17, 2010, http://www.cnn.com/HEALTH/library/burning-mouth-syndrome/DS00462.html.
"Canker Sores (Aphthous Ulcers)", 3 pages, Jan. 23, 2008, available at http://www.medicinenet.com/script/main/art.asp?articlekey=43106.
"Cellulite", 4 pages, Jul. 1, 2010, available at http://en.wikipedia.org/wiki/Cellulite.
"Dry skin", 2 pages, Aug. 20, 2010, available at http://www.mayoclinic.com/health/dry-skin/DS00560/DSECTION=causes.
Hilton, "Consumers Ill-informed about Anti-aging Options", Dermatology Times, vol. 25, pp. 58 and 61 (2004).
Oppenheim et al., "Histatins, A Novel Family of Histidine-rich Proteins in Human Parotid Secretion", J. Biol. Chem., vol. 263, pp. 7472-7477 (1988).

(Continued)

*Primary Examiner* — David Lukton
(74) *Attorney, Agent, or Firm* — Brown & Michaels, PC

(57) ABSTRACT

The current invention relates to the use of a peptide comprising an amino acid sequence in the preparation of a medicament for the regeneration of tissue, preferably for the treatment of a wound. Further the invention relates to compositions comprising such peptides, and use of said peptides in both medical and nonmedical (cosmetic) applications.

19 Claims, 4 Drawing Sheets

(56) References Cited

OTHER PUBLICATIONS

"Syneron Launches New Matrix IR™ Fractional Treatment Application for Wrinkle Treatment", 2 pages, dated May 17, 2007, available at http://investors.syneron.com/index.php?s=43&item=127.
Rudinger, Peptide Hormones, JA Parsons, Ed., 1976, pp. 1-7.
SIGMA, 2004, pp. 1-2.
Berendsen, A Glimpse of the Holy Grail?, Science, 1998, 282, pp. 642-643.
Voet et al, Biochemistry, John Wiley & Sons Inc., 1995, pp. 235-241.
Ngo et al, Computational Complexity, Protein Structure Protection, and the Levinthal Paradox, 1994, pp. 491-494.
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.
Bracci et al, Synthetic Peptides in the Form of Dendrimers Become Resistant to protease Activity, J. Biol. Chem., 2003, 278, pp. 46590-46595.
Cabras et al, Tyrosine Polysulfation of Human Salivary Histatin 1. A Post-Translational Modification Specific of the Submandibular Gland, Journal of Proteome Research, 2007, 6, pp. 2472-2480.
Merrifield, Solid Phase Synthesis, Science, 1986, pp. 341-347.
Adessi et al, Converting a Peptide into a Drug: Strategies to Improve Stability and Bioavailability, Current Medicinal Chemistry, 2002, 9, pp. 963-978.
Pini et al, Characterization of the branched antimicrobial peptide M6 by analyzing its mechanism of action and in vivo toxicity, Journal of Peptide Science, 2007, 13, pp. 393-399.
Gusman et al., Salivary Histatin 5 is an Inhibitor of Both Host and Bacterial Enzymes Implicated in Periodontal Disease, Infection and Immunity, 1402-1408 (2001).
Brewer et al., "Structure-Based Design of Potent Histatin Analogues", Biochemistry, vol. 41, pp. 5526-5536, 2002.

* cited by examiner

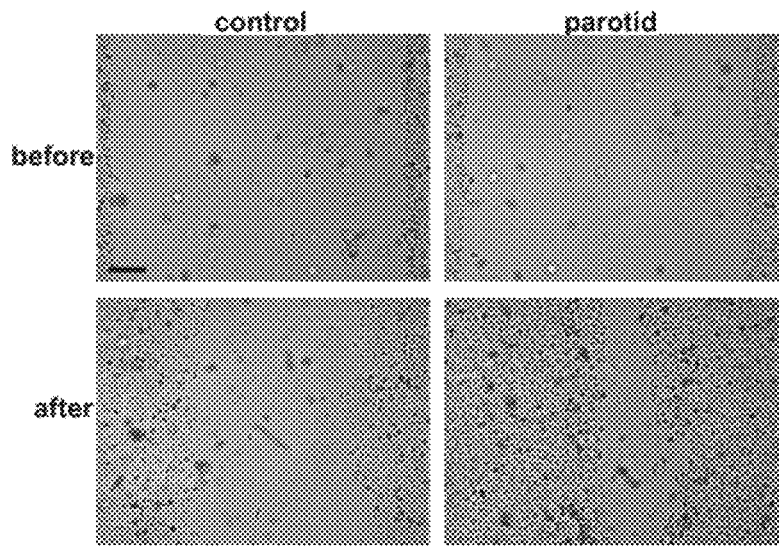
Fig. 1A
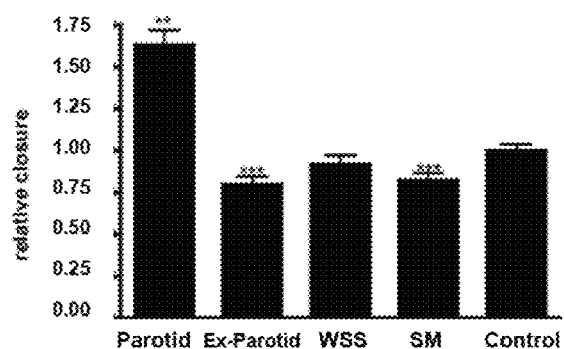
Fig. 1B
Fig. 1C
| Person | rel. closure ± st. dev. | EGF (pg/ml) |
|---|---|---|
| I | 1.43 ± 0.12 | 374 |
| II | 1.33 ± 0.21 | 852 |
| III | 1.30 ± 0.12 | 1151 |
| IV | 1.20 ± 0.18 | 948 |
| V | 1.19 ± 0.13 | 865 |
| VI | 1.16 ± 0.22 | 899 |
| Control | 1.00 ± 0.07 | 0 |
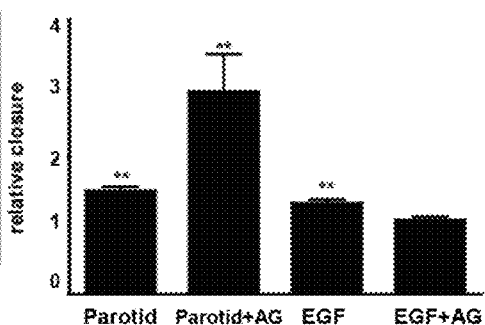
Fig. 1D

```
                         SEQUENCE LISTING

<160> NUMBER OF SEQ ID NOS: 33

<210> SEQ ID NO 1
<211> LENGTH: 7
<212> TYPE: PRT
<213> ORGANISM: Artificial Sequence
<220> FEATURE:
<223> OTHER INFORMATION: Synthetic

<400> SEQUENCE: 1

Ser Asn Tyr Leu Tyr Asp Asn
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Arg Glu Phe Pro Phe Tyr Gly Asp Tyr
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Glu Lys His His Ser His
1               5

<210> SEQ ID NO 4
<211> LENGTH: 38
<212> TYPE: PRT
<213> ORGANISM: Artificial Sequence
<220> FEATURE:
<223> OTHER INFORMATION: Synthetic

<400> SEQUENCE: 4

Asp Ser His Glu Lys Arg His His Gly Tyr Arg Arg Lys Phe His Glu
1               5                   10                  15

Lys His His Ser His Arg Glu Phe Pro Phe Tyr Gly Asp Tyr Gly Ser
            20                  25                  30

Asn Tyr Leu Tyr Asp Asn
        35

<210> SEQ ID NO 5
<211> LENGTH: 27
<212> TYPE: PRT
<213> ORGANISM: Artificial Sequence
<220> FEATURE:
<223> OTHER INFORMATION: Synthetic
```

```
<400> SEQUENCE: 5

Arg Lys Phe His Glu Lys His His Ser His Arg Glu Phe Pro Phe Tyr
1               5                   10                  15

Gly Asp Tyr Gly Ser Asn Tyr Leu Tyr Asp Asn
            20                  25

<210> SEQ ID NO 6
<211> LENGTH: 32
<212> TYPE: PRT
<213> ORGANISM: Artificial Sequence
<220> FEATURE:
<223> OTHER INFORMATION: Synthetic

<400> SEQUENCE: 6

Asp Ser His Ala Lys Arg His His Gly Tyr Lys Arg Lys Phe His Glu
1               5                   10                  15

Lys His His Ser His Arg Gly Tyr Arg Ser Asn Tyr Leu Tyr Asp Asn
            20                  25                  30

<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Glu Lys His His Ser His Arg Glu Phe Pro Phe Tyr Gly Asp Tyr
1               5                   10                  15

<210> SEQ ID NO 8
<211> LENGTH: 17
<212> TYPE: PRT
<213> ORGANISM: Artificial Sequence
<220> FEATURE:
<223> OTHER INFORMATION: Synthetic

<400> SEQUENCE: 8

Arg Glu Phe Pro Phe Tyr Gly Asp Tyr Gly Ser Asn Tyr Leu Tyr Asp
1               5                   10                  15

Asn

<210> SEQ ID NO 9
<211> LENGTH: 19
<212> TYPE: PRT
<213> ORGANISM: Artificial Sequence
<220> FEATURE:
<223> OTHER INFORMATION: Synthetic

<400> SEQUENCE: 9

Ser His Arg Glu Phe Pro Phe Tyr Gly Asp Tyr Gly Ser Asn Tyr Leu
1               5                   10                  15

Tyr Asp Asn

<210> SEQ ID NO 10
<211> LENGTH: 21
<212> TYPE: PRT
<213> ORGANISM: Artificial Sequence
<220> FEATURE:
<223> OTHER INFORMATION: Synthetic
```

```
<400> SEQUENCE: 10

His His Ser His Arg Glu Phe Pro Phe Tyr Gly Asp Tyr Gly Ser Asn
1               5                   10                  15

Tyr Leu Tyr Asp Asn
            20

<210> SEQ ID NO 11
<211> LENGTH: 23
<212> TYPE: PRT
<213> ORGANISM: Artificial Sequence
<220> FEATURE:
<223> OTHER INFORMATION: Synthetic

<400> SEQUENCE: 11

Glu Lys His His Ser His Arg Glu Phe Pro Phe Tyr Gly Asp Tyr Gly
1               5                   10                  15

Ser Asn Tyr Leu Tyr Asp Asn
            20

<210> SEQ ID NO 12
<211> LENGTH: 25
<212> TYPE: PRT
<213> ORGANISM: Artificial Sequence
<220> FEATURE:
<223> OTHER INFORMATION: Synthetic

<400> SEQUENCE: 12

Phe His Glu Lys His His Ser His Arg Glu Phe Pro Phe Tyr Gly Asp
1               5                   10                  15

Tyr Gly Ser Asn Tyr Leu Tyr Asp Asn
            20                  25

<210> SEQ ID NO 13
<211> LENGTH: 19
<212> TYPE: PRT
<213> ORGANISM: Artificial Sequence
<220> FEATURE:
<223> OTHER INFORMATION: Synthetic

<400> SEQUENCE: 13

Arg Lys Phe His Glu Lys His His Ser His Arg Glu Phe Pro Phe Tyr
1               5                   10                  15

Gly Asp Tyr

<210> SEQ ID NO 14
<211> LENGTH: 15
<212> TYPE: PRT
<213> ORGANISM: Artificial Sequence
<220> FEATURE:
<223> OTHER INFORMATION: Synthetic

<400> SEQUENCE: 14

Glu Lys His His Ser His Arg Glu Phe Pro Phe Tyr Gly Asp Tyr
1               5                   10                  15

<210> SEQ ID NO 15
<211> LENGTH: 21
<212> TYPE: PRT
<213> ORGANISM: Artificial Sequence
<220> FEATURE:
<223> OTHER INFORMATION: Synthetic
```

<400> SEQUENCE: 15

Arg Lys Phe His Glu Lys His His Ser His Arg Glu Phe Pro Phe Tyr
1               5                   10                  15

Gly Asp Tyr Gly Ser
            20

<210> SEQ ID NO 16
<211> LENGTH: 17
<212> TYPE: PRT
<213> ORGANISM: Artificial Sequence
<220> FEATURE:
<223> OTHER INFORMATION: Synthetic

<400> SEQUENCE: 16

Glu Lys His His Ser His Arg Glu Phe Pro Phe Tyr Gly Asp Tyr Gly
1               5                   10                  15

Ser

<210> SEQ ID NO 17
<211> LENGTH: 23
<212> TYPE: PRT
<213> ORGANISM: Artificial Sequence
<220> FEATURE:
<223> OTHER INFORMATION: Synthetic

<400> SEQUENCE: 17

Arg Lys Phe His Glu Lys His His Ser His Arg Glu Phe Pro Phe Tyr
1               5                   10                  15

Gly Asp Tyr Gly Ser Asn Tyr
            20

<210> SEQ ID NO 18
<211> LENGTH: 19
<212> TYPE: PRT
<213> ORGANISM: Artificial Sequence
<220> FEATURE:
<223> OTHER INFORMATION: Synthetic

<400> SEQUENCE: 18

Glu Lys His His Ser His Arg Glu Phe Pro Phe Tyr Gly Asp Tyr Gly
1               5                   10                  15

Ser Asn Tyr

<210> SEQ ID NO 19
<211> LENGTH: 25
<212> TYPE: PRT
<213> ORGANISM: Artificial Sequence
<220> FEATURE:
<223> OTHER INFORMATION: Synthetic

<400> SEQUENCE: 19

Arg Lys Phe His Glu Lys His His Ser His Arg Glu Phe Pro Phe Tyr
1               5                   10                  15

Gly Asp Tyr Gly Ser Asn Tyr Leu Tyr
            20                  25

<210> SEQ ID NO 20
<211> LENGTH: 21
<212> TYPE: PRT
<213> ORGANISM: Artificial Sequence
<220> FEATURE:
<223> OTHER INFORMATION: Synthetic

```
<400> SEQUENCE: 20

Glu Lys His His Ser His Arg Glu Phe Pro Phe Tyr Gly Asp Tyr Gly
1               5                   10                  15

Ser Asn Tyr Leu Tyr
            20

<210> SEQ ID NO 21
<211> LENGTH: 17
<212> TYPE: PRT
<213> ORGANISM: Artificial Sequence
<220> FEATURE:
<223> OTHER INFORMATION: Synthetic

<400> SEQUENCE: 21

Arg Lys Phe His Glu Lys His His Ser His Arg Glu Phe Pro Phe Tyr
1               5                   10                  15

Gly

<210> SEQ ID NO 22
<211> LENGTH: 13
<212> TYPE: PRT
<213> ORGANISM: Artificial Sequence
<220> FEATURE:
<223> OTHER INFORMATION: Synthetic

<400> SEQUENCE: 22

Glu Lys His His Ser His Arg Glu Phe Pro Phe Tyr Gly
1               5                   10

<210> SEQ ID NO 23
<211> LENGTH: 19
<212> TYPE: PRT
<213> ORGANISM: Artificial Sequence
<220> FEATURE:
<223> OTHER INFORMATION: Synthetic

<400> SEQUENCE: 23

His His Ser His Arg Glu Phe Pro Phe Tyr Gly Asp Tyr Gly Ser Asn
1               5                   10                  15

Tyr Leu Tyr

<210> SEQ ID NO 24
<211> LENGTH: 17
<212> TYPE: PRT
<213> ORGANISM: Artificial Sequence
<220> FEATURE:
<223> OTHER INFORMATION: Synthetic

<400> SEQUENCE: 24

Ser His Arg Glu Phe Pro Phe Tyr Gly Asp Tyr Gly Ser Asn Tyr Leu
1               5                   10                  15

Tyr

<210> SEQ ID NO 25
<211> LENGTH: 15
<212> TYPE: PRT
<213> ORGANISM: Artificial Sequence
<220> FEATURE:
<223> OTHER INFORMATION: Synthetic

<400> SEQUENCE: 25

Ser His Arg Glu Phe Pro Phe Tyr Gly Asp Tyr Gly Ser Asn Tyr
1               5                   10                  15
```

```
<210> SEQ ID NO 26
<211> LENGTH: 15
<212> TYPE: PRT
<213> ORGANISM: Artificial Sequence
<220> FEATURE:
<223> OTHER INFORMATION: Synthetic

<400> SEQUENCE: 26

Phe Pro Phe Tyr Gly Asp Tyr Gly Ser Asn Tyr Leu Tyr Asp Asn
1               5                   10                  15

<210> SEQ ID NO 27
<211> LENGTH: 13
<212> TYPE: PRT
<213> ORGANISM: Artificial Sequence
<220> FEATURE:
<223> OTHER INFORMATION: Synthetic

<400> SEQUENCE: 27

Phe Tyr Gly Asp Tyr Gly Ser Asn Tyr Leu Tyr Asp Asn
1               5                   10

<210> SEQ ID NO 28
<211> LENGTH: 15
<212> TYPE: PRT
<213> ORGANISM: Artificial Sequence
<220> FEATURE:
<223> OTHER INFORMATION: Synthetic

<400> SEQUENCE: 28

His His Ser His Arg Glu Phe Pro Phe Tyr Gly Asp Tyr Gly Ser
1               5                   10                  15

<210> SEQ ID NO 29
<211> LENGTH: 13
<212> TYPE: PRT
<213> ORGANISM: Artificial Sequence
<220> FEATURE:
<223> OTHER INFORMATION: Synthetic

<400> SEQUENCE: 29

Ser His Arg Glu Phe Pro Phe Tyr Gly Asp Tyr Gly Ser
1               5                   10

<210> SEQ ID NO 30
<211> LENGTH: 24
<212> TYPE: PRT
<213> ORGANISM: Artificial Sequence
<220> FEATURE:
<223> OTHER INFORMATION: Synthetic

<400> SEQUENCE: 30

Asp Ser His Ala Lys Arg His His Gly Tyr Lys Arg Lys Phe His Glu
1               5                   10                  15

Lys His His Ser His Arg Gly Tyr
            20

<210> SEQ ID NO 31
<211> LENGTH: 11
<212> TYPE: PRT
<213> ORGANISM: Artificial Sequence
<220> FEATURE:
<223> OTHER INFORMATION: Synthetic

<400> SEQUENCE: 31

Gly Asp Tyr Gly Ser Asn Tyr Leu Tyr Asp Asn
1               5                   10
```

```
<210> SEQ ID NO 32
<211> LENGTH: 17
<212> TYPE: PRT
<213> ORGANISM: Artificial Sequence
<220> FEATURE:
<223> OTHER INFORMATION: Synthetic

<400> SEQUENCE: 32

His His Ser His Arg Glu Phe Pro Phe Tyr Gly Asp Tyr Gly Ser Asn
1               5                   10                  15

Tyr

<210> SEQ ID NO 33
<211> LENGTH: 11
<212> TYPE: PRT
<213> ORGANISM: Artificial Sequence
<220> FEATURE:
<223> OTHER INFORMATION: Synthetic

<400> SEQUENCE: 33

Ser His Arg Glu Phe Pro Phe Tyr Gly Asp Tyr
1               5                   10
```

USE OF PEPTIDES FOR PROMOTING WOUND HEALING

This application is a 371 of PCT/EP2009/000241, filed Jan. 7, 2009, which claims Foreign priority to EP 08075012.8, filed Jan. 7, 2008 and Netherlands application 2002152, filed Oct. 20, 2008.

The current invention relates to the use of a peptide in the preparation of a medicament for the regeneration of tissue, for the treatment of skin, and/or for the treatment of a wound. Further the invention relates to such peptides and compositions comprising them, and to the use of said peptides in both medical and non-medical (cosmetic) applications.

Wounds inevitably happen during the lifetime of any animal being, and may be the consequence of a wide variety of occurrences, like contact with sharp or hot objects, or are seen in certain clinical conditions like diabetes.

Another clinical important example is the development of decubitus (bedsores), i.e. lesions caused by unrelieved pressure to any part of the body, especially portions over bony or cartilaginous areas. Although completely treatable if found early, without medical attention, bedsores, like any wound, can become life threatening.

In case of general reduced health status, the closure (healing) of wounds may be delayed, and can give rise to additional problems like infections, inflammation, tissue necrosis, and non-efficient wound closure becomes, again, life threatening.

It is not surprising much research has been directed to understanding the mechanisms that are important in the closure (healing) of wounds and the repair of damaged tissue, including damaged skin, as it is inevitable that rapid closure of wound is of importance for the human and animal health.

Indeed there is nowadays increased understanding of the mechanisms involved (see for example the excellent review by Martin et al, Science, Vol 276, 75 (1997)).

In general, wound healing is described as consisting of 3 phases, i.e. the inflammatory phase, the proliferative phase, and the maturational phase (referred to as acute inflammatory phase, extracellular matrix and collagen synthesis, and remodeling (Peacock, E. E., Jr., Wound Repair, 2nd edition, W B Saunders, Philadelphia (1984)).

The sequence of the healing process is initiated during an acute inflammatory phase with the deposition of provisional tissue. This is followed by re-epithelialization, collagen synthesis and deposition, fibroblast proliferation, and neovascularisation, all of which ultimately define the remodeling phase (Clark, R. A. F., J. Am. Acad. Dermatol. 13:701 (1985)).

These events are influenced by growth factors and cytokines secreted by inflammatory cells or by the cells localized at the edges of the wound (Assoian, R. K. et al., Nature (Lond.) 309:804 (1984); Nemeth, G. G. et al., "Growth Factors and Their Role in Wound and Fracture Healing," Growth Factors and Other Aspects of Wound Healing in Biological and Clinical Implications, New York (1988), pp. 1-17.

The inflammatory phase is characterized by haemostasis and inflammation. Collagen exposed during wound formation activates the clotting cascade (both the intrinsic and extrinsic pathways), initiating the inflammatory phase. Platelets, the first response cell, release multiple chemokines that help stabilize the wound through clot formation. These mediators act to control bleeding and limit the extent of injury. The second response cell to migrate to the wound, the neutrophil, is responsible for debris scavenging, complement-mediated opsonisation of bacteria, and bacteria destruction via oxidative burst mechanisms (i.e. superoxide and hydrogen peroxide formation). The macrophage is essential for wound healing. Numerous enzymes and cytokines are secreted by the macrophage, which marks the transition into the process of tissue reconstruction, i.e., the proliferative phase.

During the proliferative phase, epithelialization, angiogenesis, granulation tissue formation, and collagen deposition are the principal steps in wound healing. Epithelialization occurs early in wound repair. Angiogenesis, stimulated by for example TNF-alpha, is marked by endothelial cell migration and capillary formation. The new capillaries deliver nutrients to the wound and help maintain the granulation tissue bed. The final part of the proliferative phase is granulation tissue formation. Fibroblasts differentiate and produce ground substance and then collagen. The ground substance is deposited into the wound bed; collagen is then deposited as the wound undergoes the final phase of repair. Many different cytokines, including PDGF, insulin like growth factor (IGF), and EGF are involved in the proliferative phase of wound repair. During the maturational phase the wound undergoes contraction, ultimately resulting in a smaller amount of apparent scar tissue.

It will be obvious from the above that proper wound healing involves a complex interaction of cells and substances like cytokines working in concert. Based on fundamental research, many drugs, substances and methods of treatment have been proposed to stimulate wound healing.

Indeed, manipulation of the healing process through wound supplementation with agents that are (natural) contributors to the healing process is an appealing concept. Early experimental studies evaluating wounds supplemented with inflammatory mediators used materials extracted from cell preparations and generated encouraging results (see for example Clin Plast Surg. 2007 October; 34(4):659-71.) Recombinant technology has allowed the production of larger volumes of these mediators that can be used more practically and safely in the clinical setting.

Typical examples of such substances include for example Regranex (Becaplermin; a genetically engineered recombinant PDGF; Johnson & Johnson) Inc), a medicine that contains a platelet-derived growth factor (PDGF) and is indicated for the treatment of deep neuropathic diabetic foot ulcers.

Another example is the use of FGF's, for example FGF-2 (e.g. Curr Drug Deliv. 2006 October; 3(4):351-8), either alone, or in combination with other drugs in special carries like chitosan hydrogels.

Also hyaluronic acid as an active agent has been suggested as being useful in the treatment of skin ulcers (U.S. Pat. No. 5,897,880). In addition, topically applied fibronectin (glycoprotein found in blood plasma) has been reported as being useful for increasing the rate of wound healing in corneal wounds (Nishida, Larch Ophthalmology, 101: 1046 (1983)) and leg ulcers (Wysocki et al., Arch. Dermatol, 124: 175 (1988)).

Indeed these and other substances (like transforming growth factors (TGF-[alpha] and TGF-beta) (Science, 233: 532, 1986); insulin-like growth factors (IGF-I and II); adhesion factors, such as fibronectin, laminin and vitronectin (Ann. Rev. Biochem, 52:961, 1983), chemical substances, such as retinoids and analogous compounds thereof (Am. J. Ophthalmol., 95, 353-358, 1983; Ann. Ophthal, 19, 175-180, 1987)) have been suggested to positively influence wound healing under the circumstances studied.

EP 0575484 discloses a pharmaceutical composition for the regeneration and repair of mammalian tissues, which includes PDGF and dexamethasone. U.S. Pat. No. 5,183,805 discloses a pharmaceutical composition having the effect of regenerating tissues, which includes EGF.

Although such substances provide patients with partial wound relief, they need long healing time and fail to exhibit the optimum response to treatment. Moreover, substances like EGF are difficult to prepare, are unstable (J Pharmaco-biodyn (1991) 14: 47-52) and might quickly be inactivated when applied to a wound.

Moreover, wounds remain serious clinical problems to be solved, and alternatives useful in promoting wound healing are required, for example, alternatives that function via new and/or additional mechanisms, thereby allowing for better treatment options.

It is therefore one of the objects of the current invention to provide for a substance useful in promoting wound healing or wound closure and in the treatment of a wide variety of wounds, either alone or in combination with other substances known in the art, and that is easy to prepare in large amounts and is very stable.

Wounds typically occur on the skin. The skin is a vital organ ensuring multiple functions such as sensitive functions, protective functions from external aggressions, as well as immunological, metabolic or thermoregulatory functions. These roles are made possible due to a complex structure that associates various tissues. The skin consists of three superimposed distinct layers: epidermis, dermis and hypodermis. The epidermis is a coating epithelium, which constitutes the external structure of the skin and provides its function of protection. This function is provided by the cohesion of the epithelial cells and by the production of a filamentous and resistant protein, keratin.

Today, the cosmetic industry seeks active ingredients, which are not only able to protect and maintain skin but also active ingredients, which are able to improve its appearance as well as the well-being of the individuals who use it. A further purpose of the invention is to offer new substances and use thereof, which have preventive and curative action on the skin in such phenomena like manifestations of aging, damage to skin tissue, like wounds, and the like.

It is therefore an object of the current invention to provide for a substance that is useful in promoting wound healing and/or wound closure, that can be used in the treatment of a wide variety of wounds, or the treatment of the skin (damage of the skin) either alone or in combination with other substances known in the art, and that is easy to prepare in large amounts and is very stable.

DETAILED DESCRIPTION

It has surprisingly been found that the above-mentioned objects can be achieved by providing for the use of a peptide comprising
   a. at least one amino acid sequence of at least 6, preferably at least 7, most preferably at least 8 amino acids adjacently present in Histatin 1, 2 and/or 3; and/or
   b. at least one amino acid sequence having substitution, deletion and/or insertion of at most 3, preferably at most 2, most preferably at most 1 amino acid(s) in said amino acid sequence of at least 6, preferably at least 7, most preferably at least 8 amino acids adjacently present in Histatin 1, 2 and/or 3,
      in the preparation of a medicament for the regeneration of tissue and/or for the treatment of skin and/or for the treatment of a wound.

Preferably, the use of the peptide according to the invention is for the treatment of skin, more preferably for the treatment of a wound (either present on the skin or not).

Preferably the at least one amino acid sequence of at least 6, preferably at least 7, most preferably at least 8 amino acids is adjacently present in Histatin 1 and/or 2.

Even more preferably, as can be witnessed from the Examples, the amino acid sequence comprised in the peptide according to the invention, and adjacently present in Histatin 1, 2 and/or 3 is at least 10, 11, 12, 13, 14, or 15 amino acids long.

The term "peptide" is known in the art and relates to any compound consisting of two or more amino acids, joined by a peptide bond. Peptides can comprise of several amino acids, for example 10, 20, 50 or 100, but within the context of the current invention peptides are not limited to such numbers, but also include such larger peptides like polypeptides or proteins. However, smaller peptides are preferred, as discussed below.

The term "an amino acid sequence having substitution, deletion and/or insertion of at most 3, preferably at most 2, more preferably at most 1 amino acid" is known to the person skilled in the art.

With "substitution" is meant within the context of the current invention, the replacement of an amino acid (for example in the amino acid sequence according to any of SEQ. ID. NO. 1.-SEQ. ID. NO. 29) with another. With the term "deletion" is meant the removal of an amino acid (for example from the amino acid sequence according to any of SEQ. ID. NO. 1.-SEQ. ID. NO. 29). With the term "insertion" is meant the introduction of an amino acid at any position within the amino acid sequence (for example in any of the amino acid sequences according to SEQ. ID. NO.1-SEQ. ID. NO. 29).

Within the context of the current invention, in the case of a substitution, deletion or insertion, at most 3, preferably at most 2, more preferably at most 1 amino acid are/is substituted, deleted and/or inserted. Any substitution, deletion or insertion is allowable within the context of the current invention as long as the obtained peptide shows wound closure activity as can be determined as described in the examples (by comparison to a control).

The term "regeneration of tissue" is known to the person skilled in the art and relates to the repair, replacement, functional recovery and ultimate regeneration of damaged tissues, either in a living body (including skin), or outside the body.

Within the current invention, the peptide according to the invention can thus be used in a medicament that can be applied to a living body, for example a human or an animal, but can also be used to, outside the body, regenerate tissue, for example in the preparation of skin-grafts and the like. Once developed, such tissues are transplanted into patients to initiate the repair and rejuvenation process.

Preferably, however, the peptide is used in the preparation of a medicament for the treatment of and on a living body, for the regeneration of tissue, for the treatment of skin or eyes, or, preferably for the treatment of a wound.

The term "skin" is known to the person skilled in the art and within the context of the current invention has its normal meaning.

The term "wound" is known to the person skilled in the art and relates to damaged tissues. A wound is a type of physical trauma where the integrity of the skin or tissue is disrupted as a result from i.e. external force, bad health status, aging, exposure to sunlight, heat or chemical reaction or as a result from damage by internal physiological processes. If the outer layer of a tissue is damaged the wound is considered an open wound.

Wound closure is the process of regenerating the covering cell layers of a tissue. Promoting wound closure means creating a positive effect in the regeneration of the covering cell layers. The positive effect can be an acceleration of the process or a decrease of the damaged area of the wound.

Non-limitative examples of wounds are:

A burn wound is the injury resulting from exposure to heat, electricity, radiation (for example, sunburn and laser surgery), or caustic chemicals.

Ulcers

Wounds in Diabetes Mellitus are typically foot injuries due to numbness caused by nerve damage (diabetic neuropathy) and low blood flow to the legs and feet. The most serious injury is a foot ulcer. Diabetic foot ulcers are at very high risk of becoming infected, and sometimes they cannot be healed. Non-healing foot ulcers are a frequent cause of amputation in people with diabetes.

Decubitus wounds, decubitus (bedsores), i.e. lesions caused by unrelieved pressure to any part of the body, especially portions over bony or cartilaginous areas.

Wounds due to external force damaging the tissue

Skin wounds due to aging or the environment. This includes for example splits, dry skin, roughness of the skin and the like.

During research it was surprisingly found that when peptides comprising of at least one amino acid sequence of at least 6, preferably at least 7, most preferably at least 8 amino acids adjacently present in Histatin 1, 2 and/or 3; and/or at least one amino acid sequence having substitution, deletion and/or insertion of at most 3, preferably at most 2, most preferably at most 1 amino acid(s) in said amino acid sequence of at least 6, preferably at least 7, most preferably at least 8 amino acids adjacently present in Histatin 1,2 and/or 3, were applied to experiments to determine wound-closure (tissue regeneration/proliferation, repair of the skin), effective wound closure (repair of the skin, regeneration) was observed (see Examples).

Therefore such peptides comprising such amino acid sequences and showing effective wound closure, as can be determined as described in the methods, are very useful in the preparation of a medicament for the regeneration of tissue and/or for the treatment of skin and/or for the treatment of a wound.

Without being bound by theory it is believed that a peptide comprising an amino acid sequence according to the invention interacts with various cells involved in the skin or wound healing process, possibly by interacting with receptors present on such cells. Because of such interactions, it is believed that cell-proliferation (tissue regeneration) is induced, leading to efficient closure of for example a wound or repair of the skin. Results suggest that in contrast to EGF induced wound closure, which is $p38^{MAPK}$ dependent, the peptides according to the invention do not act via such $p38^{MAPK}$ pathway, but appears to be ERK1/2 dependent.

Histatins 1, 2 and 3 are known in the art and belong to a group of histidine-rich antimicrobial peptides, found in the saliva of man and some higher primates.

There are 12 members of this family known and they are the products of 2 different genes, Htn 1 and Htn 2. Histatin 1 and 2 are the products of Htn 1 and Histatin 3 is a product of Htn 2. Histatin 1, 2 and 3 are linear peptides that are relatively easy to produce and are therefore an improvement over growth factors for use in stimulating wound healing.

Histatins are known for their antifungal properties. It has been established that histatins bind to a receptor on the fungal cell membrane and enter the cytoplasm where they target the mitochondrion. They induce the non-lytic loss of ATP from actively respiring cells, which can induce cell death.

In addition, they have been shown to disrupt the cell cycle and lead to the generation of reactive oxygen species. Their mode of action is distinct from those exhibited by the conventional azole and polyene drugs.

Indeed, the possibility of utilizing histatins for targeting fungal infections of the oral cavity is being actively pursued with the antifungal properties of topical histatin preparations and histatin-impregnated denture acrylic being evaluated. Initial clinical studies are encouraging, having demonstrated the safety and efficacy of histatin preparations in blocking the adherence of the yeast Candida albicans to denture acrylic, retarding plaque formation and reducing the severity of gingivitis (Reviewed by Kevin Kavanagh, Susan Dowd; Journal of Pharmacy and Pharmacology Vol. 56, No. 3, pages 285 (2004).)

Interestingly, it has been found that the peptides and/or amino acid sequences according to the invention, including Histatin 1, Histatin 2 and Histatin 3, show very advantageous effects with respect to tissue regeneration, skin repair and/or wound closure. In strong contrast, and completely unexpected, Histatin 5 showed no effect with respect to tissue regeneration and/or wound closure (see Examples). Histatin 5 is therefore not included in the peptides and/or amino acids according to the current invention.

It is therefore clear that the currently found activity is for example not attributable to the generally described antifungal activity of Histatins towards for example Candida albicans, as firstly Candida albicans was not present in the methods for determining the effect of Histatins on regeneration of tissue and/or wound closure, secondly because there is no relationship between the antifungal activity of the peptides and the activity with respect to regeneration of tissue and/or wound closure, and thirdly Histatin 5, being the most active peptide towards Candida albicans has no activity towards regeneration of tissue and/or wound closure (see Examples enclosed herein).

Therefore, the peptides disclosed in for example JP06287146, including Histatin 5, are clearly distinct from the peptides according to the current invention, both in structure as well as in the mechanisms by which they might be relevant with respect to tissue regeneration, skin repair and/or wound closure. In particular, in the case the peptide according to the invention comprises an amino acid sequence according to SEQ. ID. NO.3, it is preferred it is with the proviso that such peptide is not a peptide as specifically disclosed in JP06287146.

However, in a preferred embodiment, such peptides might advantageously be combined with the peptides according to the current invention.

In a preferred embodiment there is provided for the use of a peptide comprising of at least one amino acid sequence of at least 6, preferably at least 7, most preferably at least 8 amino acids adjacently present in Histatin 1, 2 and/or 3 wherein said amino acid sequence is selected from the group consisting of SEQ. ID. NO. 1, SEQ. ID. NO. 2 and SEQ. ID. NO.3, or at least one amino acid sequence having substitution, deletion and/or insertion of at most 3, preferably at most 2, most preferably at most 1 amino acid(s) in said amino acid sequence selected from the group consisting of SEQ. ID. NO. 1, SEQ. ID. NO. 2 and SEQ. ID. NO.3.

In an even more preferred embodiment there is provided for the use of a peptide comprising of at least one amino acid sequence of at least 6, preferably at least 7, most preferably at least 8 amino acids adjacently present in Histatin 1, 2 and/or 3 wherein said amino acid sequence is according to SEQ. ID. NO. 2, or at least one amino acid sequence having substitution, deletion and/or insertion of at most 3, preferably at most 2, most preferably at most 1 amino acid(s) in said amino acid sequence according to SEQ. ID. NO. 2.

During research, in an attempt to establish the minimal requirements of the amino acid adjacently present (meaning next to each other in de sequence) in Histatin 1, 2 and/or 3, it was surprisingly found that when a peptide comprising an amino acid sequence according to SEQ. ID. NO. 1, SEQ. ID. NO. 2 and/or SEQ. ID. NO.3, and/or an amino acid sequence having substitution, deletion and/or insertion of at most 3, preferably at most 2, more preferably at most 1 amino acid in the amino acid sequence according to SEQ. ID. NO. 1, SEQ. ID. NO. 2 and/or SEQ. ID. NO.3, was applied to experiments to determine wound-closure (tissue regeneration/proliferation, repair of the skin), effective wound closure (repair of the skin, regeneration) was observed (see Examples).

In other words, the peptides according to the invention, comprising of or consisting of an amino acid sequence according to SEQ. ID. NO. 1, SEQ. ID. NO. 2 and/or SEQ. ID. NO.3 (or an amino acid sequence having substitution, deletion or insertion of at most 3, preferably at most 2, more preferably at most 1 amino acid in the amino acid sequence according to SEQ. ID. NO. 1, SEQ. ID. NO. 2 and/or SEQ. ID. NO.3), can show efficient activity towards wound-closure (skin repair, tissue regeneration/cell-proliferation) by a mechanism that is independent from the known wound-closure factor EGF. Thereby treatment of such wounds or tissue damage can be now be further improved by the provision of an alternative (or additional) mechanism that can be targeted.

Therefore also claimed is the receptor with which the peptides according to the invention, having an amino acid sequence according to the invention, interact and thereby induce wound healing; use of such receptor in the detection of compounds that might be useful in the regeneration of tissue, in particular in the treatment of skin or wounds; and use of such compounds in medicaments and the like in tissue regeneration, preferably for and in the treatment of a wound or the treatment of skin.

In another preferred embodiment, there is provided for the use of a peptide comprising an amino acid sequence selected from any of the amino acid sequences according to SEQ. ID NO. 4-SEQ ID. NO. 29, or an amino acid sequence having substitution, deletion and/or insertion of at most 3, preferably at most 2, more preferably at most 1 amino acid in the amino acid sequence according to SEQ. ID. No. 4-SEQ ID. NO 29, preferably said substitution, deletion and/or insertion not being in an amino acids sequence according to SEQ. ID. NO. 1, SEQ. ID. NO. 2, and/or SEQ. ID. NO. 3.

During experiments performed by the inventors it was observed that in addition to the above disclosed amino acid sequences, peptides having an amino acids sequence according to SEQ. ID. NO. 4-SEQ ID. NO. 29 show beneficial effects with respect to regeneration of tissue, wound closure and or treatment of the skin.

As can be seen in the examples, the peptides or amino acid sequences have been modified by the removal of 2, 4, 6, 8, 12 etc amino acids in comparison to for example the amino acid sequence SEQ. ID. NO 5 (Histatin 2). Moreover, all these sequences showed beneficial effects in the tests performed. It will thus be appreciated by the skilled person that in addition to those amino acids sequences according to SEQ. ID. NO 4-SEQ. ID. NO. 29, in addition also the amino acids wherein 1, 3, 5, 7, 9, 11, 13, etc. amino acids have been removed in comparison to SEQ. ID. NO. 5, for example by removal of the tripeptide RKF, the pentapeptide RKFHE, etc. from the N-terminus of SEQ. ID. NO. 5, or by the removal of the tripeptide YDN, or the pentapeptide YLYDN, etc. from the C-terminus of SEQ. ID. NO. 5, are also included as amino acids that can be comprised (or form) the peptides according to the invention. Obviously, the removal of amino acids can also be from both the N-terminus and the C-terminus, as long as the remaining peptide shows activity with regard to wound closure, for example as determined in the Examples.

In another preferred embodiment, the peptide according to the invention comprises or preferably consists of an amino acid sequence selected from the group consisting of SEQ. ID. NO. 4, SEQ. ID. NO. 5, SEQ. ID. NO. 6, or parts or fragments thereof and which show wound closure activity.

The peptide according to SEQ. ID NO. 4 is also known as Histatin 1; the peptide according to SEQ. ID NO. 5 is also known as Histatin 2; the peptide according to SEQ. ID NO 6 is also known as Histatin 3.

As will be appreciated, and based upon the current disclosure, the skilled person will without any further inventive skill be capable of determining the wound closure activity of fragments or parts of amino acid sequences selected from the group consisting of SEQ. ID. NO. 4, SEQ. ID. NO. 5, and/or SEQ. ID. NO. 6, for example as is described in detail in the Examples. It will be understood that such parts or fragments are part of the current invention. Preferably, said parts or fragments are derived from the amino acid sequence according to SEQ. ID. NO. 5.

As will be understood by the skilled person, the amino acids and the peptide comprising such amino acid sequences as disclosed in the current invention include those in which at least one functional grouping (in particular the amine and carboxylic groupings) are protected with a protective grouping. As the peptide according to the invention is to be applied to tissue, skin or wound, it is beneficial, for resistance to degradation, to use a protected form of the peptide. The form of protection must obviously be a biologically compatible form and must be compatible with cosmetic use or the field of pharmaceuticals. Many biologically compatible forms of protection can be considered, they are well known to the person skilled in the art, such as for example the acylation or the acetylation of the amino-terminal, cyclization or the amidation or the esterfication of the carboxy-terminal. Thus, the invention also concerns a use such as previously defined and characterized by the fact that the peptide is in a protected form.

Peptides, objects of this patent, can be obtained either by traditional chemical synthesis (for example as described in the Examples, or in solid phase or in homogeneous liquid phase), or by enzymatic synthesis (Kullman et al., J. Biol. Chem. 1980, 225, 8234) from constitutive amino acids or from their derivatives. Peptides relating to the invention can also be obtained by fermentation of a strain of bacteria, modified or not, by genetic engineering to produce peptides of the sequence, as previously indicated, and their fragments.

Also, there is provided for nucleotides (DNA, cDNA, RNA, etc.) encoding for a peptide comprising an amino acid sequence according to the invention, and use thereof for providing for the peptides according to the invention.

In another embodiment, the peptide comprises or consists of at least 8, more preferably at least 10, even more preferably at least 20, most preferably at least 27 amino acids.

It has been found that if the peptide according to the invention comprises or consists of at least 8, more preferably at least 10, even more preferably at least 20, most preferably at least 27 amino acids, there is provided for a peptide, which shows good activity with regard to tissue regeneration, skin treatment and/or wound closure.

It is believed that, in addition to for example the amino acid sequence according to SEQ. ID. NO 1-SEQ. ID. NO. 29, or an amino acid sequence having substitution, deletion or insertion of at most 3, preferably at most 2, more preferably at most 1 amino acid in the amino acid sequence according to SEQ.

ID. NO 1-SEQ. ID. NO. 29, the additional amino acids contribute positively to the interaction of the peptide with the cells involved or present in tissue regeneration, skin repair and/or wound closure.

It will therefore be understood by the person skilled in the art that any amount of additional amino acids (next to the amino acids sequences according to the invention) might be present in the peptide according to the invention as long as this does not substantially negatively influence the activity of the peptide in closing a wound, for example as determined in the methods as described in the examples.

In another preferred embodiment there is provided that the peptide for use in the current invention comprises 8-40 amino acids, more preferably 12-39 amino acids, even more preferably 27-38 amino acids.

As has been discussed above, it was found that in particular peptides comprising 8-40 amino acids, more preferably 12-39 amino acids, even more preferably 27-38 amino acids are in particular efficient in the regeneration of tissue, in skin treatment and in particular in closing a wound, as described in the examples.

It is believed that, in addition to for example the amino acid sequence according to SEQ. ID. NO 1-29, or an amino acid sequence having substitution, deletion or insertion of at most 3, preferably at most 2, more preferably at most 1 amino acid in the amino acid sequence according to SEQ. ID. NO 1-29, the additional amino acids contribute positively to the interaction of the peptide with the cells involved or present in tissue regeneration, skin repair and/or wound closure.

Although, as mentioned above, the peptides my comprise of more amino acids than described in the above ranges of amino acids, it is however believed that when the peptide comprises of too many amino acids, interaction of the peptide according to the invention with cells and receptors might be negatively influenced, thereby reducing the efficacy of the peptide according to the invention in tissue regeneration, skin treatment and/or treatment of a wound (wound closure). Therefore, it is preferred that the peptide according to the invention comprises at most no more than (about) 100 amino acids.

It will therefore be understood by the person skilled in the art that any amount of additional amino acids might be present in the peptide according to the invention as long as this does not substantially negatively influence the activity of the peptide in closing a wound (in regeneration of tissue or in treatment of skin), for example in the methods as described in the examples.

In another preferred embodiment there is provided that the peptide according to the invention is an L-peptide, or in other words, the peptide according to the invention is made up of L-amino acids.

Indeed, with the term "L-peptide" is meant a peptide wherein all amino acids are in the L-form, i.e. in the form as they are normally produced in a living body.

Nineteen of the essential twenty amino acids have the property of "chirality" or handedness. The only achiral essential amino acid is glycine. To describe a chiral compound, the prefixes D and L are used to refer to the configuration of the molecule around its chiral centre. The chiral centre of an amino acid is the alpha carbon, and whether an amino acid is of the D configuration or the L configuration depends upon the stereoisomeric conventions established by Emil Fisher. A chiral amino acid can exist as stereoisomers, which are identical chemical structures that are mirror images of each other. Both stereoisomers are often referred to as an enantiomeric pair, and a stereoisomer is often referred to as an enantiomer, which is a nonsuperimposable mirror image of the other stereoisomer/enantiomer.

All of the naturally occurring chiral amino acids exist in the L configuration, and are referred to generally as L-amino acids. The stereoisomer of each chiral amino acid in the L-configuration is referred to as a D-amino acid.

It was found that in case D-amino acids were used instead of L-amino acids in the peptide according to the invention, activity of the peptide according to the invention in tissue regeneration and/or wound closure was significantly reduced in comparison to when the natural occurring L-amino acids made up a peptide according to the invention.

It is believed that a peptide comprising of only L-amino acids provides for better interaction with cells and or receptors involved in tissue regeneration and/or wound closure.

In another embodiment, there is provided for the use according to the invention wherein the peptide is a cyclic peptide.

It has been found that when, for example, a peptide comprising an amino acid sequence according to SEQ. ID. NO. 4 was provided in cyclic form, the activity of such cyclic form of the peptide is dramatically increased in comparison to the linear form. In other words, in order to achieve the same skin repair effect, wound healing or wound closure effect, or the same effect with regard to tissue regeneration, as for example can be determined with the methods described in the examples, a (much) lower concentration of a cyclic peptide according to the invention can be used in comparison to the same peptide in linear form. Alternatively, when using the same concentration of a linear form of a peptide according to the invention of a cyclic form of a peptide according to the invention, dramatically increased skin repair, wound closure, tissue regeneration can be established with the cyclic peptide in comparison to the linear form of the same peptide (and as for example given in any of SEQ. ID. NO.1-29).

In other words, in a preferred embodiment there is provided for a peptide according to the invention in cyclic form, more in particular the cyclic peptide comprises an amino acid sequence according to any of SEQ. ID. NO. 1-SEQ. ID NO. 29.

The person skilled in the art knows how to provide for a cyclic peptide, and many suitable methods have been described in the art. For example, U.S. Pat. No. 6,555,650 discloses a method for providing cyclic analogs of histatins having substantial homology to His 5 (the method for preparing such cyclic forms can be used within the context of the current invention).

In addition, Goncalves et. al. (Tetrahedron 61 (2005) 7789-7795) describes a method that can be applied for forming cyclic peptides according to the current invention. In short, in such method a linear peptide is constructed using standard Fmoc chemistry and on-resin cyclization was enabled after selective deprotection of the C-terminal group with hydrazine/DMF.

It is believed that the improved characteristics of such cyclic peptides in comparison to the linear peptides, might be due to increased metabolic stability, potency, receptor selectivity and/or bioavailability. It will therefore be understood by the skilled person that the cyclic peptides are not limited to the cyclic peptide as shown in the examples, but include any cyclic peptide comprising an amino acid sequence selected from any of the amino acid sequences according to SEQ. ID NO. 1-SEQ ID. NO. 29, or an amino acid sequence having substitution, deletion and/or insertion of at most 3, preferably at most 2, more preferably at most 1 amino acid in the amino acid sequence according to SEQ. ID NO. 1-SEQ ID. NO. 29, preferably said substitution, deletion and/or insertion not being in the amino acids sequence according to SEQ. ID. NO. 1, SEQ. ID. NO. 2, and/or SEQ. ID. NO. 3.

Also included are those cyclic peptides comprising an amino acid sequence according to SEQ. ID. NO. 1, SEQ. ID. NO. 2, and/or SEQ. ID. NO. 3, or an amino acid sequence having substitution, deletion and/or insertion of at most 3, preferably at most 2, more preferably at most 1 amino acid in the amino acid sequence according to SEQ. ID. NO. 1, SEQ. ID. NO. 2, and/or SEQ. ID. NO. 3.

In addition, as explained above, also included are those cyclic peptides comprising an amino acid sequence wherein 1, 3, 5, 7, 9, 11, 13, etc. amino acids have been removed in comparison to SEQ. ID. NO. 5, for example by removal of the tripeptide RKF, the pentapeptide RKFHE, etc. from the N-terminus of SEQ. ID. NO. 5, or by the removal of the tripeptide YDN, or the pentapeptide YLYDN, etc. from the C-terminus of SEQ. ID. NO. 5, or by removal from both the N-terminus and the C-terminus of SEQ. ID. NO. 5. These amino acids sequences can be comprised in a cyclic peptide according to the invention.

Therefore, in a further embodiment of the invention there is provided for the use of a cyclic peptide according to the invention wherein the cyclic peptide comprises an amino acid sequence selected from any of the amino acid sequences according to SEQ. ID NO. 1-SEQ ID. No. 29, or an amino acid sequence having substitution, deletion and/or insertion of at most 3, preferably at most 2, more preferably at most 1 amino acid in the amino acid sequence according to SEQ. ID. NO. 1-SEQ ID. NO 29, preferably said substitution, deletion and/or insertion not being in the amino acids sequence according to SEQ. ID. NO. 1, SEQ. ID. NO. 2, and/or SEQ. ID. NO. 3

Indeed it has been found that when a cyclic peptide comprising an amino acid sequence according to the invention is compared to the same peptide but in linear form, the concentration of the cyclic peptide might be 5, even 10, even 100 times lower in comparison to the linear form of the same peptide (for example a linear form of the amino acid sequence according to SEQ. ID. NO. 4 (Histatin 1)).

Therefore, there is provided for use according to the invention of a cyclic peptide according to the invention wherein said cyclic peptide has a relative wound closure activity that is equal to the relative wound closure activity of a linear peptide according to SEQ. ID. NO. 4 (HIS1) at a concentration of 1 µM (in the method according to the Examples), at a concentration of the said cyclic peptide that is at least 5, more preferably at least 10, even more preferably at least 100 times lower. In particular the said relative wound closure activity is measured according to the method of Example 1.

Any skilled person is capable of determining the relative wound closure activity using the methods as described in the examples and can thus easily determine the activity of any linear peptide of cyclic peptide according to the invention and compare such results.

In another embodiment of the invention, the peptide according to the invention is a dimer or mulitmer, each monomer forming the dimer or multimer preferably consisting of (being formed by) an amino acid sequence as defined above, even more preferably each monomer consisting of an amino acid sequence according to any of SEQ. ID. NO. 1-SEQ ID. NO. 29.

The skilled person understand what the term "dimer" or "multimer" within the context of the current invention is intended to indicate, i.e., a distinct part of the peptide according to the invention in combination with another distinct part, either directly linked in a peptide bond or indirectly via a linking sequence or a cross-linker. The parts can be linked either in a parallel fashion ($X_1$-$X_2$-$X_3$- . . . $Xn$—Y—$X_1$-$X_2$-$X_3$- . . . $X_n$), or, and thus included in the current invention, in an antiparallel fashion ($X_1$-$X_2$-$X_3$- . . . $X_n$—Y—$X_n$-$X_{n-1}$-$X_{n-2}$- . . . $X_1$) in which $X_n$ indicates the amino acid residue at position 1 (starting from the N-terminus) and Y denotes the cross-linking between the two "monomers". In other words, a peptide according to the invention may comprise any fusion of at least two amino acid sequences according to the invention, each amino acid sequence according to the invention forming a "monomer" within the context of the invention.

Further, and in addition to the example described above, such peptide may comprise additional amino acids, preferably being according to an amino acid according to the invention, forming a further monomer within the context of the invention.

Preferably, the peptide is a dimer comprising two identical monomers according to the invention, and as described above, for example both monomers within the context of the invention having an amino acid sequence according to SEQ. ID. NO. 1-SEQ ID. NO. 29.

As will be understood by the skilled person, also included in the current invention are those peptides according to the invention that are conjugated. Within the current invention "conjugation" is to be construed as the binding of a peptide according to the invention to another material, in particular to a carrier, for example a polystyrene bead, BSA, an antibody or a delivery vehicle like. Thus, in another embodiment there is provided a peptide according to the invention that is conjugated.

With respect to the observed increase in activity of the above-discussed cyclic form of a peptide according to the invention, it is believed this might at least partially be due to the constraining of the conformational freedom of the linear peptides by the cyclization. It will therefore be understood by the skilled person that also comprised are peptides according to the invention that have been constrained in their conformational freedom, in addition to cyclic peptides. The person skilled in the art is aware of methods constraining the conformational freedom of peptides according to the invention, for example a method wherein said peptide has been constrained in its conformational freedom by cross-linking or by the formation of sulphur-sulphur bridges. For example by the CLIPS technology as e.g. described by Lesauteur et al (JBC, 270, 6564-6569). This is achieved by substitution of non-critical residues with cysteine or by insertion of cysteine residues in non-critical positions of the molecule. Subsequently cyclization can be conducted by oxidative dimerization (by flushing with oxygen or air) or by treatment with diiodomethane, or by reaction with fast small aromatic scaffolds like α,α'-dibromo-m-xylene α,α'-dibromo-m-xylene.

In another preferred embodiment, in addition to the peptide according to the invention, further a growth factor, preferably selected from the group consisting of platelet derived growth factor (PDGF), insulin like-growth factor (IGF), transforming growth factor (TGF), hepatocyte growth factor (HGF), epidermal growth factor (EGF), fibroblast growth factor (FGF), is used in the preparation of the medicament, or in the treatment of skin or wound.

As already discussed above, the peptides according to the invention contribute to tissue regeneration and/or wound closure and/or skin treatment by a mechanism different from that of for example EGF. It is therefore with advantage to combine compounds/drugs and the like with the peptides according to the invention and that contribute to regeneration of tissue and/or closure of the wound (wound treatment) and/or skin treatment by mechanisms that are, preferably, independent from the mechanism by which the peptides according to the invention act. By combining said different mechanisms in one treatment, better results are obtainable.

In another preferred embodiment, there is provided for the use according to any of the previous clauses wherein the treatment of the skin is for the treatment or prevention of aging of the skin, cellulites, dry skin, splits, wounds or wherein the wound is an internal wound, an oral wound, a skin wound, an external wound, an ulcer, and/or a decubitus wound, damage to the eye, a wound in the eye, for example conjunctiva. Other conditions that can be treated with the peptides according to the invention include oral ulcers, oral aphthous lesions, Burning mouth syndrome, Burning tongue, psoriasis, eczema, and hair loss.

These types of skin damages and wounds are known to the person skilled in the art. An internal wound is a wound present in the body, for example due to a surgical incision. An oral wound is a wound present in the oral cavity. A skin wound is a wound present in the skin. An external wound is to be understood as a wound that is visible and accessible from outside the body. An ulcer is a lesion on the surface of the skin or a mucous surface. A decubitus wound is a wound or ulceration caused by prolonged pressure on the skin and tissues when one stay in one position for a long period of time, such as lying in bed. The bony areas of the body are the most frequently affected sites, which become ischemic under sustained and constant pressure. Aging of the skin is the change in appearance of the skin due to time or exposure to the environment or the health status of an individual. Cellulites is the definition used in cosmetics relating to a wobbly or dimpled appearance of the skin (orange skin in Dutch).

In a more preferred embodiment of the invention, the method is used for the treatment of a skin wound. Skin wounds can be wounds in the epidermis or dermis of the skin. There are several types of wounds in which the skin or tissue may be in need of repair: abrasions, lacerations, incisions, punctures and avulsions and burns. Use of a peptide according to the invention can improve the general health status of the skin. In another preferred embodiment of the invention, the method is used for the treatment of an oral wound. Oral wounds are wounds in any part of the oral cavity wherein the oral mucosa is damaged. In another preferred embodiment of the invention, the method is used for the treatment of an internal wound. Internal wounds are wounds wherein cell layers of endodermal or mesodermal origin are damaged. Examples are wounds in arteries or venes, peritoneum or pericardium.

In another preferred embodiment there is provided for the use of the peptide according to the invention in the preparation of a medicament and wherein the medicament has an ionic strength of at least 20 mM, more preferably 50 mM, even more preferably 100 mM, most preferably at least 120 mM, before of after application to a wound.

The term ionic strength is known to the person skilled in the art, and can for example be determined according to PAC, 1996, 68, 977 (IUPAC;) It has surprisingly been found that in contrast to for example any antifungal activity, activity with respect to tissue regeneration and/or wound closure is maintained at such levels of ionic strength.

For example, when the peptide according to the invention is applied to a wound which excretes some exudate, it will be active with respect to tissue regeneration and/or wound closure, whereas, due to the presence of a too high an ionic strength (due to ions being present in the exudate), peptides like Histatin 5 will not be functioning as a antifungal at such concentrations (see Examples).

In another aspect of the current invention, there is provided a composition comprising a peptide according to the invention, and as described above, characterized in that the composition further comprises at least one pharmaceutically acceptable excipient.

In a preferred embodiment, the excipient is pharmaceutically acceptable in the treatment of a wound, i.e. does not negatively interfere with the treatment of the wound and/or the regeneration of tissue.

In addition, the composition according to the invention can further comprise a growth factor, preferably selected from the group consisting of platelet derived growth factor (PDGF), insulin like-growth factor (IGF), transforming growth factor (TGF), hepatocyte growth factor (HGF), epidermal growth factor (EGF), fibroblast growth factor (FGF), for the reasons discussed above.

The compositions according to the discussion can suitable be used in the treatments as described above.

In another preferred embodiment, the composition is in the form of a solution, an ointment, a salve, a balsam, a tincture, an elixir, a plaster, a bandage, a dressing material, an alginate dressing, a topical solution, an infusion, or a surgical rinse solution.

Preferably the composition comprises the peptide according to the invention in an amount of about 0.0001 to 500 mg of the peptide per milliliter of gram of the medicament.

In case of the medicament/composition being in an aqueous form, i.e. a solution or an ointment, the pH of the medicament is between pH 3.0 and pH 9.0. In another preferred embodiment, said composition has an ionic strength of at least 20 mM, more preferably 50 mM, even more preferably 100 mM, most preferably at least 120 mM, before of after application to a wound, and as discussed above.

In another aspect of the current invention there is provided for a method for the treatment of skin or treatment of a wound comprising the step of applying to said skin or wound an amino acid a peptide or compositions as defined herein. The said method is very useful in the treatment of wounds, skin, or in the regeneration of tissue, and as described herein. Preferably the medicament comprising the peptide according to the invention comprises about 0.0001 to 500 mg of the peptide per milliliter of gram of the medicament. In case of the medicament in an aqueous form, i.e. a solution or an ointment, the pH of the medicament is between pH 3.0 and pH 9.0.

In another aspect of the current invention there is provided for the use of the peptides according to the invention is the cosmetic (non-medical) treatment of the skin. It has been found that even if there is no medical need for the treatment of the skin, application of a peptide according to the invention to for example aged skin, or skin being subject to environmental stress (i.e. air pollution) advantageously shows improvement in the structure and appearance of the skin.

The above mentioned peptide can be solubilised in one or several cosmetically or pharmaceutically acceptable solvents such as water, ethanol, propanol or isopropanol, propylene glycol, butylene glycol, dipropylene glycol, ethoxylated or propoxylated diglycols, cyclic polyols or any combinations of these solvents, or are solubilised in a cosmetic or pharmaceutical vector such as liposomes or are adsorbed on powdered organic polymers, mineral supports such as talc and bentonites, and more generally solubilised in, or fixed on, any cosmetically or pharmaceutically acceptable vectors. It is of course obvious that the peptide according to the invention can be used alone or in partnership with at least another active agent, in or for the preparation of a cosmetic and/or dermatological and/or pharmaceutical composition. The peptide according to the invention can favorably be used as skin care product and treatment agent for the skin. Skin care product and treatment agent refer to agents which in a general way have a repairing and revitalizing activity allowing, inter alia, the skin and/or superficial body growths to better react to the aggressions which they can be subjected to.

It will be understood that the peptide according to the invention can be used alone or in association with at least another active agent. In the composition according to the invention, the peptide can be a mixture of peptide derivatives and/or consisting of amino acids derivatives.

The peptides according to the invention can therefore suitable be used in cosmetic preparation intended for application to the skin.

It will be understood by the person skilled in the art that in addition to amino acids, the peptide may further contain such commonly used groups like signal-peptides or chemical groups like protection groups like tBoc, tags, of even be associated with or included in for example nano-particles and liposomes, for example carrying an additional drug, for example useful in the treatment of wounds. Peptides that are chemically modified such as by glycosylation, pegylation, acetylation, methylation, ubiquitination, hydroxylation, palmitoylation, phosphorylation can also be used as long as these modifications do not hamper the wound closing properties and/or tissue regeneration and or treatment of the skin.

In another aspect there is provided for an amino acid sequence, peptide or composition as defined in any of the previous claims, preferably a peptide comprising or consisting of an amino acid sequence according to any of SEQ. ID. NO. 1-SEQ. ID. NO. 29, or an amino acid sequence having substitution, deletion and/or insertion of at most 3, preferably at most 2, more preferably at most 1 amino acid in the amino acid sequence according to SEQ. ID. NO.1-SEQ ID. NO. 29.

Also provided is the amino acid sequence, peptide or composition according to the invention for use as a medicament. In particular provided are amino acid sequence, peptide or composition according to the invention in the treatment of skin, wound or in tissue regeneration, preferably a peptide comprising or consisting of a amino acid sequence according to any of SEQ. ID. NO. 1-SEQ. ID. NO 29.

BRIEF DESCRIPTION OF THE DRAWINGS

FIG. 1A illustrates a typical in vitro scratch wound closure experiment in which parotid saliva or a peptide according to the invention, after 16 hours, induces wound closure of an epithelial monolayer. Different salivary secretions, 30% (v/v) in SFM, were tested in this model with saliva buffer as a negative control. FIG. 1B is a graph showing parotid saliva was the only secretion exhibiting induced wound closure. Even the other secretions inhibited wound closure. Human whole stimulated saliva mainly consists of parotid saliva. FIG. 1C shows the results of wound closure and EGF concentrations in six different persons. All but one person showed significant induced wound closure. Furthermore, EGF concentrations do not correspond to the degree of wound closure, indicating that different factor(s) are responsible. FIG. 1D is a graph showing that, to fully rebut EGF's role as wound closure inducing factor in human parotid saliva, the activation of its receptor was inhibited. With the receptor blocked the induction by parotid saliva not only remained, but even was boosted. This indicates responsibility of this receptor for the closure in the control and thus the background in our assay, most likely caused by endogenous production of ligands for the EGF receptor. Of course, EGF, at a concentration of 5 ng/ml, was able to induce wound closure with rates comparable to that of parotid saliva (FIG. 1D). Addition of AG1478 however, abolished the effect as expected.

EXAMPLES

Example 1

1. Experimental Conditions 1.1 Cell Culture

Figure 2:
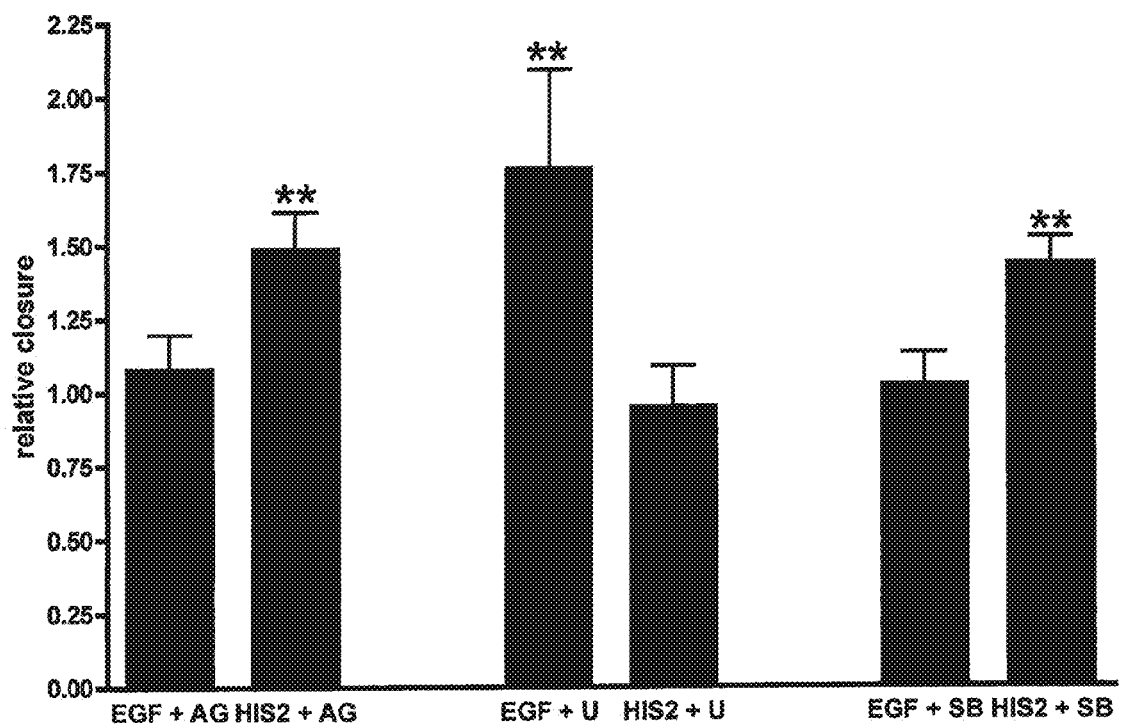
FIG. 2 is a graph showing that the EGFR independent induced wound closure of saliva as shown in FIG. 1 is affirmed by doing the same for Histatin 2. Also confirmed are the previously mentioned studies, which show EGF induced wound closure is $p38^{MAPK}$ dependent. Histatin 2 induced wound closure however, is not $p38^{MAPK}$ but appears ERK1/2 dependent.

The human buccal epithelial cell line TR146 (Rupniak et al; J Natl Cancer Inst. 1985 October; 75(4):621-35) was kindly provided by Cancer Research UK. Cells were grown in Dulbecco's modified Eagle medium with 4.5 g/l glucose (Invitrogen), 10% FCS (HyClone) and 100 U/ml penicillin, 100 mg/ml streptomycin, and 250 ng/ml amphotericinB (Antibiotic antimyotic solution, Sigma,), at 37° C., 95% humidity and 5% CO2. Cells were maintained until near confluence and then briefly treated with 0.25% trypsin-EDTA 1× (Invitrogen) to detach them, counted in a hepacytometer and seeded into new flasks or multi-well plates at the required cell density of about 1.5×10×5 cells/well.

1.2 Saliva Collection

Saliva was collected as previously described (Veerman et al., 1996 Eur J Oral Sci. 104:346-52.). Human whole stimulated saliva (WSS) was collected by chewing on a piece of parafilm. Parotid saliva collected with the aid of a Lashley cup positioned over Stensons duct into a polypropylene tube. The fluid accumulating in the mouth during the collection of the parotid secretion (designated ex-parotid saliva), which is mainly composed of the combined secretions of the submandibular and sublingual glands, was collected simultaneously by spitting into an ice-cooled vessel. Submandibular saliva (SM) was collected using a custom-made collection device placed in the floor of the mouth over the exits of ducts of the submandibular glands. Before use, all saliva samples were sterilized using a 0.45 µm pore rezist filter (Whatman). Saliva buffer was assembled based on the properties of stimulated parotid saliva with pH=7.3 and consisted of 30 mM Na2CO3, 10 mM KCl, 6 mM K2HPO4, 3 mM KSCN, 1 mM CaCl2 and 0.1 mM MgCl2. The high molecular weight salivary mucin MUC5B was isolated by ultracentrifugation and gel filtration chromatography, as previously described (Veerman et al., 1991, Arch Oral Biol. 36:923-32.).

1.3 EGF Enzyme-Linked Immuno Sorbent Assay (ELISA)

EGF concentrations in saliva were measured by ELISA using human EGF cytoset™ kit, following manufacturer's instructions (Biosource).

1.4 In Vitro Wound Healing Experiments

Wound assays were performed as previously described (Matthay et al., 1993, J Cell Sci. 106 (Pt 3):869-78). In brief, cells were grown in 12-well plates until confluence, and then were serum deprived for 24 hours in keratinocyte serum free medium (SFM (Invitrogen)). In each well a scratch was made in the cellular monolayer using a sterile tip. The wounded monolayer was washed with SFM to remove cellular debris, and the following conditions were applied:
(i) Whole saliva and salivary secretions applied in 30% (v/v) in SFM. As a negative control 30% (v/v) saliva buffer was used.
(ii) (ii) rhEGF (Invitrogen) as a positive control
(iii) rp-HPLC fractions containing salivary proteins;
(iv) synthetic peptides: the experiments with isolated proteins and synthetic peptides were performed in full SFM.

The width of the wound area was determined microscopically immediately after wound creation and at approximately 16 hours after wounding. The relative closure was calculated by relating the closure to that of the negative control.

For inhibitor studies; directly after wounding cells were exposed to inhibitors of ERK1/2 (U0126, 5 µM, LC Laboratories), EGFR (AG1478, 1 µM, Calbiochem), and p38 MAPK (SB203580, 5 µM; LC Laboratories). Experiments were done in quadruplicate and analyzed using One-way ANOVA to determine significance with additional LSD post hoc test, $P<0.05$ was considered significant.

1.5 HPLC Chromatography of Parotid Saliva and Identification of Proteins

Parotid saliva (2 ml) from one donor was subjected to reversed phase high-performance liquid chromatography (RP-HPLC) on a C8 column by using a RP-HPLC system (Jasco). The fractions that exhibited wound closure properties were pooled and reconstituted in 1 ml HPLC-grade water and subjected to RP-HPLC chromatography on a C18 column. Resulting fractions that induced wound closure, were analyzed with ion trap mass spectrometry with a LCQ Deca XP (Thermo Finnigan).

1.6 Peptide Synthesis

Synthetic peptides were synthesized using by solid phase peptide synthesis using Fmoc chemistry with a MilliGen 9050 peptide synthesizer (Milligen-Biosearch), FITC labeling, purification and authenticity confirmation as previously described (den Hertog et al., 2005, Biochem J. 388:689-95).

1.7 Proliferation Assay

Approximately $1 \times 10^4$ cells were seeded in 24 well plates and incubated overnight. Cells were treated with Karyomax™ (Invitrogen) for 6 hours. After washing with SFM, they were incubated for 24 h and pulsed with 1 µCi of [methyl-3H]-thymidine for 24 h at 37° C. Then cells were washed with ice cold PBS, 100% methanol and 5% TCA. The acid-insoluble material was dissolved in 0.5 M NaOH at room temperature and the level of radioactivity was counted using a liquid scintillation counter (Packard). Values were converted from absolute counts to a percentage of the control.

1.8 Microscopy and Imaging

Microscope: Leica DM IL PLAN 4-40× magnification, 0.5 lens; camera: Leica DFC320; and acquisition software: Leica IM500. Images were quantified using Adobe Photoshop CS3. Additionally, brightness/contrast levels of the co-localization studies were altered with Adobe Photoshop CS3. FITC labeled histatin was incubated with the cells for two hours. PI was added to check for membrane disruptive dependent internalization. 100 mM Azide was used for 1 hour. Cells were trypsinized as described above. Co-localization studies were performed using Mitotracker (Invitrogen) and Lysotracker (Invitrogen) following manufacturer's instructions.

2. Results 2.1 There is no correlation between wound closure properties of saliva and different salivary secretions vs. saliva buffer and their EGF concentrations. Since the majority of studies on wound healing dealt with saliva from rodents, it was first affirmed that human salivary secretions indeed accelerate wound closure in the model used herein. Some studies have found salivary substances enhancing migration and proliferation, whereas other studies found factors in saliva which inhibited attachment and migration, such as MUC5B. Although, most of these studies use isolated proteins, which makes it difficult to interpret its context.

FIG. 1A illustrates a typical in vitro scratch wound closure experiment in which parotid saliva, after 16 hours, induces wound closure of an epithelial monolayer. Different salivary secretions, 30% (v/v) in SFM, were tested in this model with saliva buffer as a negative control. Parotid saliva was the only secretion exhibiting induced wound closure (FIG. 1B).

Next, the role of EGF's in parotid induced wound closure was studied. Wound closure and EGF concentrations of six different persons was studied (FIG. 1C). All but one person showed significant induced wound closure, and EGF concentrations does appear not to correspond to the degree of wound closure, indicating that different factor(s) are involved. To fully rebut EGF's role as wound closure inducing factor in human parotid saliva we inhibited the activation of its receptor with 1 µM AG1478 (FIG. 1D). With the receptor blocked the induction by parotid saliva not only remained, but even was boosted. This indicates responsibility of this receptor for the closure in the control and thus the background in our assay, most likely caused by endogenous production of ligands for the EGF receptor. Of course, EGF, at a concentration of 5 ng/ml, was able to induce wound closure with rates comparable to that of parotid saliva (FIG. 1D). Addition of AG1478 however, abolished the effect as expected.

2.2 Histatins are the Wound Closing Factors in Saliva

After EGF was ruled out as the main component for parotid induced wound closure, RP-HPLC was used to separate parotid saliva and the activity of the pooled fractions was determined. First we found activity only in the $2^{nd}$ fraction. In this fraction, the bulk of proteins present in parotid saliva, including amylase, is absent, which was confirmed by SDS page gel electrophoresis. The $2^{nd}$ fraction could further be separated into two fractions, designated fraction 4 and 5. Fraction 5 was found to have biological activity. Fraction 5 was further separated using a C18 column, and consisted of 4 proteins, which were analyzed with ion trap mass spectrometry with a LCQ Deca XP (Thermo Finnigan). Biological activity was solely found in designated peak 6. By ion trap mass MS it was found that peak 6 contained a product of the Htn1 gene. Htn1 is responsible for Histatins 1 and 2, and Htn2 for Histatins 3 and 5.

2.3 Potency of Histatin induced wound closure, stereospecificity of Histatin 2, candidacidal activities of the different histatins. Next the potency of the different Histatins in both wound healing as their candidacidal activities was studied. Histatins are known for their antimicrobial activity. Histatin 5 generally has the lowest $LC_{50}$ (concentration in which 50% of the micro-organisms are killed), and the killing activity is reduced with increasing ionic strength.

We tested synthesized Histatins 1, 2, 3, 5 and the enantiomer of Histatin 2 (designated D-Histatin 2) on wound closure and candidacidal activities. In the test concentrations of 1, 5, 10, 30 and 50 µg/ml of the peptides were tested. Results shows that optimal concentration were, for Histatin 1, 10-30 µg/ml, for Histatin 2, 5-10 µg/ml, and for Histatin 3, 30-50 µg/ml. (Table 1). Histatins 1, 2 and 3 all induce wound closure, D-Histatin 2 and Histatin 5 do not.

| Peptide | Sequence | SEQ ID NO: | Wound closure rel. clos. ± SD | Candicidal activity LC50 ± SD 1 mM PPB | SFM |
|---|---|---|---|---|---|
| Histatin 1 | DSHEKRHHGYRRKFHEKHHSHREFPFYGDYGSNYLYDN | (SEQ ID NO: 4) | 1.22 ± 0.12* | 6.0 ± 0.3 | >100 |
| Histatin 2 | RKFHEKHHSHREFPFYGDYGSNYLYDN | (SEQ ID NO: 5) | 1.36 ± 0.13* | 13.8 ± 1.9 | >100 |
| D-Histatin 2 | RKFHEKHHSHREFPFYGDYGSNYLYDN | (SEQ ID NO: 5) | 0.99 ± 0.14 | 10.7 ± 1.2 | >100 |
| Histatin 3 | DSHAKRHHGYKRKFHEKHHSHR.....G.YRSNYLY DN | (SEQ ID NO: 6) | 1.21 ± 0.12* | 1.1 ± 0.1 | >100 |
| Histatin 5 | DSHAKRHHGYKRKFHEKHHSHR.....G.Y | (SEQ ID NO: 30) | 1.04 ± 0.11 | 2.3 ± 0.1 | >100 |
| EGF | | | 1.41 ± 0.12* | | |

Histatin 2 has the most potent induction of wound closure, which does not significantly differ from the optimal EGF induced wound closure. Also, lowest concentration of Histatin 2 is needed to achieve this closure. Interestingly, D-Histatin 2 does not exhibit wound closure induction, indicating at least partial stereo-specific activation of processes inducing wound closure.

Also, Histatin 5 does not show induced wound closure, implying a necessity of parts of particular amino acids in the peptide. Contradictorily, the candidacidal activity in 1 mM PPB shows no stereo-specificity of Histatin 2 and point out Histatins 3 and 5 as the most potent, i.e. the lowest $LC_{50}$. Additionally, in SFM (150 mM) no candidacidal activity whatsoever was could be demonstrated. Also, at an ionic strength of 50 mM, which is in the physiological range of saliva already proved enough to completely abolish the candidacidal effect of histatins (data not shown). Altogether the results of the experiments in Table 1 clearly show that the structural features involved in the candidacidal of histatin 5 and wound healing properties of histatin 1, 2 and 3 are completely different.

2.4 Further Observations

In Candida Histatin 5 is internalized and associates with the energized mitochondrion. Given the abovementioned discrepancy between C. albicans and epithelial cells we were very interested whether histatins become internalized and where in the cells they accumulate. In co-accordance with their wound healing properties Histatins 1, 2 and 3 are internalized, and D-Histatin 2 and Histatin 5 are not (data not shown). $NaN_3$ inhibits the function of cytochrome c oxidase by binding irreversibly to the heme cofactor. Thus, $NaN_3$ treatment lead us to conclude that the internalization energy dependent. Trypsin treatment shows us that membrane proteins are essential for the internalization. Which, in addition to the stereo-specificity, is indicating a receptor mediated process. We used mitochondria and acidic lysosome specific markers to elucidate histatin's fate once it is internalized Erk1/2 Responsible for Histatin Induced Wound Closure A mechanism has been proposed in which in vitro wound closure is coordinated by two mitogen-activated protein kinase (MAPK) cascades. The $p38^{MAPK}$ cascade is responsible for migration and the extracellular signal-regulated kinases (ERK1/2) cascade for proliferation. Furthermore, blockage of one activates the other, indicating cross-talk. Another paper, which affirmed this model, showed that epidermal growth factor (EGF) stimulated migration required continuous presence of the ligand. Of course it is very interesting to study which pathways are conducted when cells are stimulated with histatins. In FIG. 2 we affirm the in FIG. 1 shown EGFR independent induced wound closure of saliva by doing the same for Histatin 2. We also confirm the previously mentioned studies, which show EGF induced wound closure is $p38^{MAPK}$ dependent. Histatin 2 induced wound closure however, is not $p38^{MAPK}$ but appears ERK1/2 dependent. These findings also suggest receptor mediated activation. Histatins are relatively cheap to manufacture, and thus can be a target of becoming a clinical wound inducing substance.

Example 2

Testing of Various Peptides

Peptides were synthesized as described above and tested in the "wound closure assay" (In vitro wound healing experiments) according to Example 1 in a concentration of 10 µg/ml.

Figure 3:
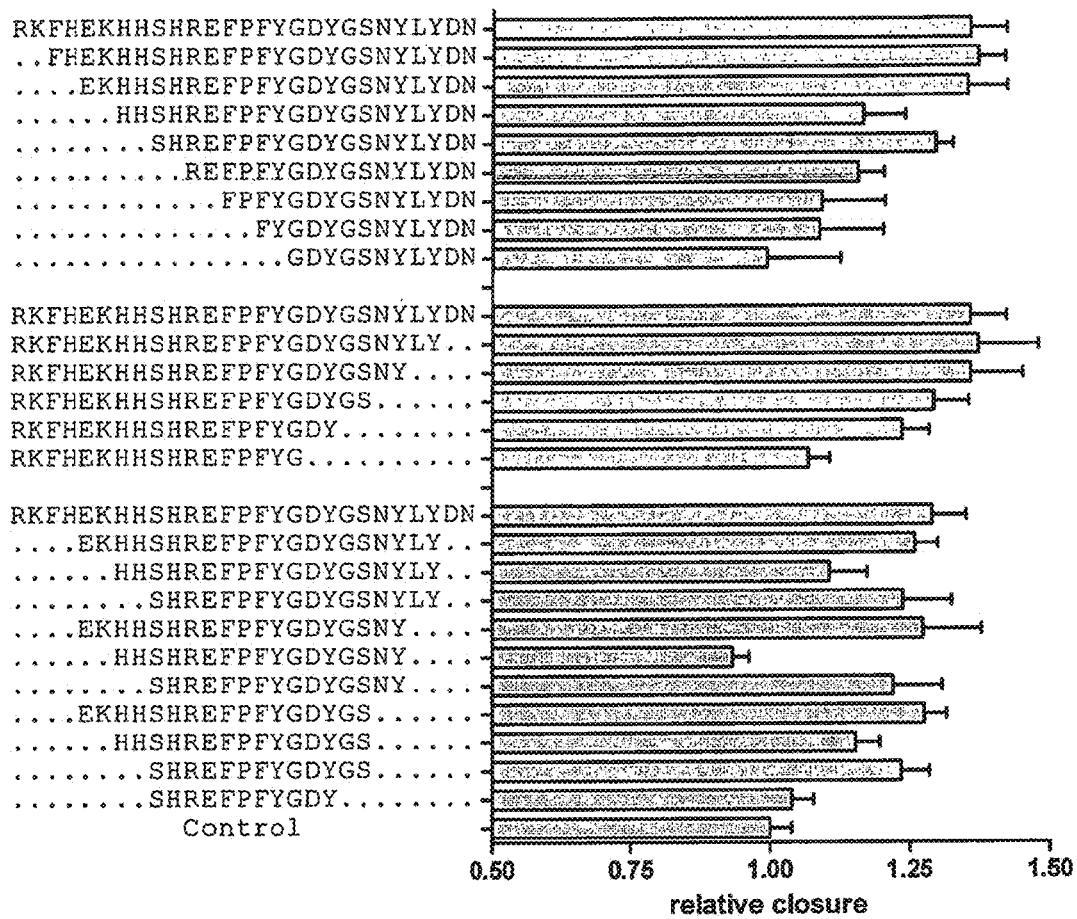
FIG. 3 is a graph showing the results of various amino acids and/or peptides (SEQ ID NOs: 5, 12, 11, 10, 9, 8, 26, 31, 5, 19, 17, 15, 13, 21, 5, 20, 23, 24, 18, 32, 25, 16, 28, 29, and 33 in descending order) according to the invention in wound closure experiments.

FIG. 3 shows both the peptides tested and the results obtained. In addition to the mentioned amino acid sequences, peptides were tested wherein the first four amino acids at the N-terminal were removes (RKFH). The removal thereof did not influence the activity in the assay. Results were compared to control. The results show that the amino acids according to the invention show good activity in the assays.

Example 3

Cyclic Peptides

A cyclic peptide having the amino acid sequence according to SEQ. ID. NO. 4, Histatin 1, was produced using a WANG LL resin available from Novabiochem (EMD Biosciences), described in detail in Novabiochem Letter 2/06 (EMD Biosciences Inc. P.O. Box 12087 La Jolla, Calif. 92039-2087). Cyclization of the linear peptide attached to the resin was according to Goncalves et. al. (Tetrahedron 61 (2005) 7789-7795). In short, after completion of the peptide assembly, the resin was treated with 2% hydrazine/DMF at room temperature for 3 min. The treatment was repeated two more times, and the partially protected resin was thoroughly washed with DMF. For the intramolecular cyclization 0.3-3 M equiv of each benzotriazol-1-yloxy-tris(pyrrolidino)phosphonium hexa-fluorophosphate (PyBOP) and HOBt were used in the presence of 6 M equiv of diisopropylethylamine (DIEA) for 72 h. The obtained product was fractionated by HPLC chromatography and the resulting fractions tested.

Next, the cyclic peptide was compared to the linear peptide in the in vitro wound healing experiments as described under Example 1. Results are shown in FIG. 4.

Figure 4:
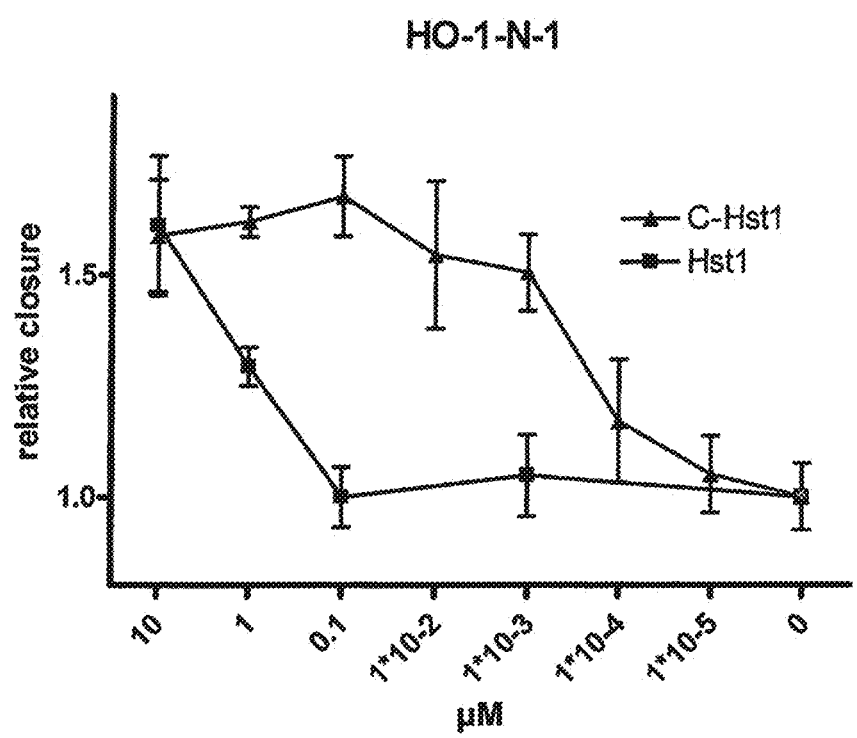
FIG. 4 is a graph showing the relative wound closure activity of either the cyclic peptide (C-Hst1) or the liner peptide (Hst1) at different concentrations of each of the peptides.

FIG. 4 shows the relative wound closure activity of either the cyclic peptide (C-Hst1) or the linear peptide (Hst1) at different concentration of each of the peptides. Even at a concentration of $1*10^{-3}$ µM C-HST1, relative wound closure is still 1.5, whereas wound closure activity of HST1 has dropped to just above 1 (Relative wound closure activity of 1 is the wound closure activity when no peptide is added to the assay described above). The results clearly show that cyclic peptides according to the invention, having an amino acid sequence according to the invention, show remarkably increased activity in comparison to the linear peptides according to the invention, even when the concentration is 5, 10 or even 100 times lower in comparison to the linear peptide.

The invention claimed is:

1. A method for the treatment of a wound, wherein the wound is a result of a physical trauma, comprising applying to the wound of a subject in need thereof a peptide comprising at least six contiguous residues of the amino acid sequence of SEQ ID NO: 2 or a variant peptide thereof in which one amino acid residue is substituted, deleted or inserted within said at least six contiguous residues, wherein applying the peptide to the wound promotes closure of the wound.

2. The method of claim 1, wherein the peptide comprises the amino acid sequence selected from the group consisting of SEQ ID NO: 4, and SEQ ID NO: 5.

3. The method of claim 1, wherein the peptide comprises the amino acid sequence selected from the group consisting of SEQ ID NOs: 7-20, 23-25, and 28-29.

4. The method of claim 1, wherein the peptide is at least 10 amino acid residues in length.

5. The method of claim 1, wherein the peptide is at least 20 amino acid residues in length.

6. The method of claim 1, wherein the peptide is in the range of 12 to 39 amino acid residues in length.

7. The method of claim 1, wherein the peptide is not more than about 100 residues in length.

8. The method of claim 1, wherein the peptide is a L-peptide.

9. The method of claim 1, wherein the peptide is a cyclic peptide.

10. The method of claim 9, wherein the cyclic peptide comprises an amino acid sequence selected from the group consisting of SEQ ID NOs: 2, 4, 5, 7-20, 23-25, and 28-29 or a variant thereof in which one amino acid residue in any of SEQ ID NOs: 4, 5, 7-20, 23-25, and 28-29 is substituted, deleted or inserted and the one residue substitution, deletion or insertion is not within a subsequence of SEQ ID NO: 2.

11. The method of claim 9, wherein the cyclic peptide has a relative wound closure activity that is equal to the relative wound closure activity of 1 µM concentration of the linear peptide of SEQ ID NO: 4 but at a concentration of cyclic peptide that is at least 5 times lower.

12. The method of claim 1, wherein the peptide is a dimer or multimer of a monomer of (i) said at least six contiguous residues of SEQ ID NO: 5 or (ii) a variant of (i) in which one amino acid residue is substituted, deleted or inserted within said at least six contiguous residues.

13. The method of claim 1, wherein the peptide is a dimer or multimer of a monomer consisting of an amino acid sequence selected from the group consisting of SEQ ID NOs: 2, 4, 5, 7-20, 23-25, and 28-29.

14. The method of claim 1, wherein the peptide is conjugated.

15. The method of claim 1, wherein the conformational freedom of the peptide has been constrained by chemical treatment.

16. The method of claim 15, wherein conformational freedom of the peptide has been constrained by cross-linking or disulfide bonds.

17. The method of claim 1, wherein a growth factor is applied with the peptide, wherein the growth factor is selected from the group consisting of platelet derived growth factor (PDGF), insulin like-growth factor (IGF), transforming growth factor (TGF), hepatocyte growth factor (HGF), epidermal growth factor (EGF), and fibroblast growth factor (FGF).

18. The method of claim 1, wherein the physical trauma is selected from the group consisting of: an abrasion, a laceration, an incision, a puncture, an avulsion, and a burn.

19. A method for promoting closure of a wound, wherein the wound is a result of a physical trauma, comprising applying to the wound of a subject in need thereof a peptide comprising at least six contiguous residues of the amino acid sequence of SEQ ID NO: 2 or a variant peptide thereof in which one amino acid residue is substituted, deleted or inserted within said at least six contiguous residues, and promoting closure of the wound.

* * * * *